United States Patent [19]

Emini et al.

[11] Patent Number: 4,761,470

[45] Date of Patent: Aug. 2, 1988

[54] IMMUNOGENIC SYNTHETIC PEPTIDE CAPABLE OF ELICITING HERPES SIMPLEX VIRUS NEUTRALIZING ANTIBODY

[75] Inventors: Emilio A. Emini, Paoli; Vivian M. Larson, Harleysville, both of Pa.; Joshua S. Boger, Westfield, N.J.

[73] Assignee: Merck & Co., Inc., Rahway, N.J.

[21] Appl. No.: 36,651

[22] Filed: Apr. 10, 1987

Related U.S. Application Data

[63] Continuation-in-part of Ser. No. 809,452, Dec. 16, 1985, abandoned.

[51] Int. Cl.$^4$ .............................................. C07K 7/08
[52] U.S. Cl. .................................... 530/326; 530/345
[58] Field of Search ................................. 530/326, 345

[56] References Cited

U.S. PATENT DOCUMENTS

| | | | |
|---|---|---|---|
| 4,317,811 | 3/1982 | Bertland et al. | 424/89 |
| 4,374,127 | 2/1983 | Larson et al. | 424/89 |
| 4,452,734 | 6/1984 | Larson et al. | 424/89 |
| 4,540,669 | 9/1985 | Bertland et al. | 424/89 |
| 4,572,896 | 2/1986 | Hampar et al. | 435/240 |
| 4,618,578 | 10/1986 | Burke et al. | 435/172.3 |

OTHER PUBLICATIONS

Virology, 135, 301–314, (1984), Bzik, et al.
J. Gen. Virol., (1982), 58, 217–222.
Emo Journal, 3, (1984), 3135–41, Everets.

*Primary Examiner*—Delbert R. Phillips
*Attorney, Agent, or Firm*—Donald J. Perrella; Hesna J. Pfeiffer

[57] ABSTRACT

A synthetic peptide, containing the predicted amino acid residues 64 to 77 of the herpes simplex virus type 1 (HSV1) gB structural glycoprotein open reading frame, a synthetic subunit immunogen that stimulates an immune response against HSV1 and which, when prepared, and chemically-conjugated to a protein carrier molecule, and inoculated into test animals, gives rise to a specific anti-peptide IgG response, such that these anti-peptide antibodies react with a purified HSV-specific structural glycoprotein preparation and are capable of neutralizing the infectivity of HSV1.

6 Claims, No Drawings

IMMUNOGENIC SYNTHETIC PEPTIDE CAPABLE OF ELICITING HERPES SIMPLEX VIRUS NEUTRALIZING ANTIBODY

The present application is a continuation-in-part of U.S. patent application, Ser. No. 809,452, filed Dec. 16, 1985, now abandoned.

BACKGROUND OF THE INVENTION

Herpes simplex virus type 1 (HSV1) is predominantly transmitted by the oral-respiratory route and is responsible for such human clinical conditions as herpes labialis, acute gingivostomatitis, keratoconjunctivitis, and encephalitis. Following primary infection with the virus, a latent infection is usually established. This latency is responsible for the recurrent nature of HSV-associated clinical disease.

No vaccine currently exists for prevention of herpes simplex virus-associated disease in humans. The potential oncogenic nature of the virus' nucleic acid precludes the development and use of a classic live or killed vaccine. However, a synthetic immunogen would serve as a useful vaccine substrate.

The predicted amino acid sequence of the HSV1 glycoprotein B (gB), a major virion surface structural component, is known (D. J. Bzik et al., Virology 133: 301–314, 1984).

It is accordingly the object of the present invention to define a synthetic peptide, containing amino acid residues from the HSV1 gB structural protein, which specifically induces HSV1 neutralizing antibodies. This peptide serves as a vaccine immunogen for HSV1.

SUMMARY OF THE INVENTION

The present invention is directed to peptides, containing the predicted amino acid residues 64 to 77 of the HSV1 gB glycoprotein open reading frame, which are useful as synthetic immunogens to specifically unduce the production of HSV1-neutralizing antibodies. When synthesized and chemically-conjugated to carrier protein molecules, these peptide-carrier conjugates elicit, in animals, antibodies which bind to purified HSV glycoprotein preparations and which neutralize the infectivity of HSV1.

DETAILED DESCRIPTION OF THE INVENTION

I. Selection of the Peptide Sequence

An immunogenic peptide from the HSV1 gB structural protein has been identified. The peptide comprises a core of the following sequence wherein the number indicates the position of the amino acids in the HSV1 gB open reading frame:

```
65                  70                    75
Asp—Pro—Lys—Pro—Lys—Lys—Asn—Lys—Lys—Pro—Lys
``` and may be extended on either side by amino acids contained in the natural sequence up to and including the following sequence:

```
64  65              70                  75      77
Gly—Asp—Pro—Lys—Pro—Lys—Lys—Asn—Lys—Lys—Pro—Lys—Asn—Pro
```

In addition, to each sequence may be added one or more linker amino acids, such as Lys (free or side-chain acylated with a photoreactive group), Tyr, Cys, Glu, or Asp, at either or both N or C terminus to facilitate the conjugation to a carrier. In addition, the sequence may include one or more spacer amino acids of, for example, Gly, Ala or Nle, included between the natural sequence and the linker amino acids, or at the N or C terminus itself. The peptide terminal may be free amino, amino acylated with N-benzoylbenzoyl (or other photoreactive group), or N-acetyl (or other alkyl carboxyl) and free carboxy or amide.

Specifically, the invention is directed to an immunogenic synthetic peptide which has the sequence:

$$\text{A-B-D-Gly-Asp-Pro-Lys-Pro-Lys-Lys-Asn-Lys-Lys-Pro-Lys-Asn-Pro-E-G-J-K} \quad (I),$$

wherein:
- A is amino, amino-p-benzoylbenzoyl, N-acetyl, or carboxyl
- B is absent, Tyr or Lys;
- D is absent or Nle;
- E is absent, Thr, Cys or Nle;
- G is absent or Pro;
- J is absent or Pro; and
- K is amino or carboxyl;

or a pharmaceutically-acceptable salt thereof.

Preferred sequences of these peptides then include those from herpes simplex type 1 gB surface protein, comprising the amino acid sequence:

$$\text{A-Thr-Gly-Asp-Pro-Lys-Pro-Lys-Lys-Asn-Lys-Lys-Pro-Lys-Asn-Pro-Thr-Pro-Pro-K},$$

and particularly:
1. Ac-Tyr-Nle-Gly-Asp-Pro-Lys-Pro-Lys-Lys-Asn-Lys-Lys-Pro-Lys-Asn-Pro-Cys-NH$_2$;
2. Ac-Lys-Nle-Gly-Asp-Pro-Lys-Pro-Lys-Lys-Asn-Lys-Lys-Pro-Lys-Asn-Pro-Nle-NH$_2$; and
3. Ac-Lys(BB)-Nle-Gly-Asp-Pro-Lys-Pro-Lys-Lys-Asn-Lys-Lys-Pro-Lys-Asn-Pro-Nle-NH$_2$, where Cys may be either free thiol (for linking to carrier) or as an Acm derivative, and BB represents p-benzoyl-benzoyl.

The pharmaceutically-acceptable salts of the peptides of Formula I (in the form of water- or oil-soluble or dispersible products) include the conventional non-toxic salts or the quaternary ammonium salts of these peptides, which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexlamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

| Abbreviations | |
|---|---|
| Abbreviation | Meaning |
| Ala | L-alanine |
| Arg | L-arginine |
| Asn | L-asparagine |
| Asp | L-aspartic acid |
| Cys | L-cysteine |
| Gln | L-glutamine |
| Glu | L-glutamic acid |
| Gly | glycine |
| His | L-histidine |
| Ile | L-isoleucine |
| Leu | L-leucine |
| Lys | L-lysine |
| Met | L-methionine |
| Nle | L-norleucine |
| Phe | L-phenylalanine |
| Pro | L-proline |
| Ser | L-serine |
| Thr | L-threonine |
| Trp | L-tryptophan |
| Tyr | L-tyrosine |
| Val | L-valine |
| Ac | acetyl |
| Acm | acetamidomethyl |
| Boc | tert-butyloxycarbonyl |
| Bzl | benzyl |
| 2,6-$Cl_2$—CBZ | 2,6-dichlorobenzyl |
| CBZ | benzyloxycarbonyl |
| 2-Cl—CBZ | 2-chlorobenzyloxycarbonyl |
| DNP | 2,4-dinitrophenyl |
| $NO_2$ | nitro |
| DCC | dicyclohexylcarbodiimide |
| DMF | dimethylformamide |
| TFA | trifluoroacetic acid |
| TEA | triethylamine |
| HBT | 1-hydroxybenzotriazole |

II. Peptide Synthesis

The peptides described here are made by solid phase sequential synthesis, beginning from the C-terminus, according to procedures described by Barany & Merrifield (in "The Peptides", Vol. 2, Ed., E. Gross & J. Meienhofer, pp. 1–284, Academic Press, New York, N.Y., 1980), using a Beckman 990B peptide synthesizer to carry out the operations according to the attached programs. The starting polymer beads are a p-methylbenzhydrylamine-functionalized polystyrene-divinylbenzene (PS-DVB, 1% cross-linked, see Stewart et al., "Peptides 1976", Ed., A. Loffet, pp. 285–290, Editions de l'Universite de Bruxelles, Belgium, 1976), when the C-terminus is to be an amide. The C-terminal amino acid of the desired sequence is attached, as its N-protected and side chain-protected (when necessary) derivative, to the resin as an amide according to the same procedures used for chain elongation. Initial amino acid loading is 0.1–1.1 mmoles/g of starting resin. Remaining amine sites are blocked using acetic anhydride/pyridine before proceeding with chain elongation.

After the amino-protecting group is removed, using 25–40% TFA in $CH_2Cl_2$, containing 1% EDT, or 4N HCl in dioxane, the protected derivative of the next amino acid is added, along with a coupling reagent, if necessary such as DCC, along with additives such as HBT. The amino acid reactant may be employed in the form of carboxyl-activated amino acid such as an nitrophenyl ester, an amino acid azide, and the like. A coupling reaction may be repeated in order to obtain complete reaction. Deprotection and addition of successive amino acids is performed until the desired sequence is formed. Coupling reactions using DCC-activated Asn use two equivalents of HBT to suppress side-chain dehydration.

The selection of protecting groups is, in part, dictated by coupling conditions, in part by the amino acid and peptide components involved in the reaction. Aminoprotecting groups ordinarily employed include those well known in the art, for example, urethane protecting substituents such as benzyloxycarbonyl ("CBZ"), tert-butyloxycarbonyl ("Boc"), and the like. Boc is preferred for protecting the alpha-amino group in the amino acids undergoing reaction at the carboxyl end of said amino acid. The Boc protecting group is easily removed using TFA, as mentioned above, or other acids such as HCl (3M in dioxane).

The epsilon-amino group of Lys can be protected by the CBZ group, or preferably by 2-Cl-CBZ group. The OH of Tyr is protected preferably using the 2,6-$Cl_2$-Bzl group, although the Bzl group may be used where the Tyr residue is toward the N-terminal side of the desired sequence. The OH group of Thr and Ser can be protected by the Bzl group. Arg is protected with the nitro group. Asp is protected as its benzyl ester. Cys is protected as the Acm derivative. These groups are relatively stable to the action of TFA used to remove the Boc group at each step. After the peptide sequence is formed, these protecting groups, except for Acm, can be removed by the action of HF or by hydrogenation. The Acm group can be removed from the free peptide by Hg to give the free Cys or by $I_2$ to give a disulfide.

After the peptide has been formed on the resin, it may be removed by several well-known methods appropriate to the particular resin, preferably using liquid HF in a low-high procedure as sescribed by Tam et al., *Int. J. Peptide Protein Res.*, 21: 57–65, 1983, and references therein. Purification of the peptides uses Sephadex sizing chromatography (G-15, G-25, and G-50c depending on the peptide size) in either 50% or 2N acetic acid, and reverse phase HPLC on C-18 reverse phase columns, when necessary, using gradient elutions from dilute TFA (0.1%) or trimethylamine phosphate (PH 3.2) or acetonitrile.

Peptide products are characterized primarily by amino acid analyses performed on a Beckman 121MB or Beckman 6300 analyzer after 70 hours hydrolyses in 6N HCl. The peptide product is checked by HPLC and is found generally to be 50–70% homogeneous.

III. Conjugation Procedures

In order to enhance peptide immunogenicity, the peptide described here is usually covalently linked ("conjugated") to a larger molecule which serves as a carrier. Carriers can include proteins such as heterologous serum albumins, keyhole limpet hemocyanin, diphtheria toxoid, etc. or synthetic polymers such as Poly(D-Glu,D-Lys). Attachment of the peptide to the carrier can be by one of several methods, including linking through a peptide Lys using glutaraldehyde (Reichlin, *Methods Enzymol.* 70: 159–165, 1980) or DCC procedures (for example, Atassi et al., *Biochem. Biophys.*

*Acta* 670: 300–302, 1981), through a Peptide Asp or Glu using DCC (Bauminger et al., *Methods Enzymol* 70: 151–159, 1980), through a peptide Tyr using bis-diazotized benzidine (Walter et al., *Proc. Nat. Acad. Sci. USA* 77: 5197–5200, 1980), through photochemical attachment sites (Parker et al., *Cold Spring Harbor Symposium - Modern Aoproaches to Vaccines*, Ed. Chanock & Lerner, Cold Spring Harbor Press, New York, 1984), or through a peptide Cys (Liu et al., Biochem. 18: 690–697, 1979). Peptide carrier conjugates are separated from excess free peptide by dialysis or gel filtration. The level of loading of the peptide on the carrier can be determined either using a radioactive tracer to establish the loading level in a particular procedure, or by quantitative amino acid analysis of the conjugate, in comparison with the unloaded carrier. It is convenient, when using the latter technique, to incorporate a unique non-natural amino acid into the peptide, at the N-terminal or C-terminal side, such as Nle, which can then serve as a quantitative marker for peptide incorporation, as measured by amino acid analysis of the conjugate. This Nle can also function as a spacer between the antigenic site and any amino acid incorporated to facilitate attachment, such as Cys, Lys, or Tyr, as described above.

The peptide of the present invention, either free or conjugated, may be administered in a physiologically-acceptable carrier to a susceptible mammalian species to protect against viral disease, particularly against DNA viruses including herpes viruses, and most particularly against HSV1 disease.

The invention is further defined by reference to the following examples, which are intended to be illustrative and not limiting.

EXAMPLE 1

Synthesis:
N-Acetyl-L-Tyrosyl-L-Norleucyl-Glycyl-L-Aspartyl-L-Prolyl-L-Lysyl-L-Prolyl-L-Lysyl-L-Lysyl-L-Asparaginyl-L-Lysyl-L-Lysyl-L-Proly-L-Lysly-L-Asparaginyl-L-Prolyl-L-(S-Acetamidomethyl)-Cysteinyl Amide The title sequence was synthesized on a Beckman 990B peptide synthesizer on p-methylbenzhydrylamine resin according to general solid phase procedures as described by G. Barany & R. B. Merrifield (in "The Peptides", Vol. 2, Ed., E. Gross & J. Meienhofer, pp. 1–284, Academic Press, New York, N.Y., 1980). Specifically, the initial Boc-(Acm)-Cys was loaded onto the p-methylbenzhydrylamine resin (nominal amine content of 0.414 mmol N per g), using Program 2 (run twice), followed by capping of any unreacted amine sites using acetic anhydride/pyridine (10 equivalents each) and Program 4. This starting resin was analyzed by elemental analysis and found to contain approximately 0.3 mmol/g of Boc-(Acm)-Cys, as judged by the S analysis. Synthesis was continued on a 1 mmol scale (3.33 g Boc-(Acm)-Cys-NH-Resin), adding successive protected amino acids to the growing N-terminus, according to Programs 1 (for Boc-removal and coupling), 2 (for recoupling), and 3 & 4 (for terminal acetylation, using 10 equivalents of acetic anhydride/pyridine). Boc-protection was used throughout for alpha-amino temporary protection. Asp side chains were protected as the O-benzyl ether. Tyr side chain was protected as the 2,6-Cl$_2$-benzyl ether. The epsilon-amino group of Lys was protected by the 2-Cl-CBZ group. All couplings and recouplings used a 2.5 equivalent excess of amino acid over peptide chain. Two recouplings were done at every step. Couplings and recouplings used DCC with HBT added to each amino acid solution (each 2.5 equivalents vs. the nominal starting resin). The completed resin, dried in vacuo, weighed 6.0 g.

A 3.0 g portion of this peptide resin was treated in a "low-high" HF deprotection/removal, according to the procedures described by J. P. Tam, W. F. Heath, & R. B. Merrifield (*Int. J. Peptide Protein Res.*, 21, 57–65, 1983). Briefly, the resin was placed in the vessel of a standard HF-Reaction Apparatus (Peninsula Laboratories). To the resin was added 1.5 ml m-cresol and 6.5 ml dimethyl sulfide. This was cooled to −78° C. and 2.5 ml HF was condensed into the reaction. This was stirred at 0° C. for 2 hours, and the HF and DMS were removed under high vacuum conditions for 30 minutes at 0° C. with liquid nitrogen trapping. After trituration with ether and drying, the resin was placed back in the HF apparatus with 1.5 ml m-cresol, cooled to −78° C., and 20 ml HF was condensed in. This was stirred at 0° C. for 1 hour, after which the HF was removed by high vacuum at 0° C. The resin and product were washed and decanted with petroleum ether, triturated with ethyl acetate, and filtered. The solid was then suspended in 50 ml of 50% acetic acid, solubilizing the peptide product, and placed directly onto a G-15 Sephadex chromatography column prepared and eluted with 50% acetic acid. The column showed two large peaks, and the material eluting just after the void volume was combined and stripped to a film.

This crude peptide material was applied to a G-50 Sephadex chromatography column, packed and eluted with 50% acetic acid. Fractions were examined by reverse phase HPLC (C-18 column, 0.1% TFA/acetonitrile gradient elution), and fractions containing the major 210 nm absorbing material were combined and evaporated. This material was freeze-dried, followed by reverse phase HPLC on C18 Zorbax ODS 21.2 mm×25 cm column using gradient elution from 95% dilute TFA (0.1%) aqueous buffer to 95% acetonitrile. Amino acid analysis gave: Lys 5.1 (incomplete hydrolysis of lys-lys makes this number too small), Asx (Asp and Asn) 3.4, Gly 1.08, Tyr 1.02, Nle 1.04, Pro 9.2 (interference with Cys degradation makes this number too large). The product is 60% peptide content (the rest being salts and water) based on a molecular weight of 2066.14.

EXAMPLE 2

Synthesis of Bovine Serum Albumin Conjugate of
Ac-Tyr-Nle-Gly-Asp-Pro-Lys-Pro-Lys-Lys-Asn-Lys-Lys-Pro-Lys-Asn-Pro-Cys-NH$_2$ The title peptide sequence was conjugated to bovine serum albumin (BSA) derivatized with m-maleimidobenzoyl-N-hydroxysuccinimide ester (MBS) according to the procedures described by F. T. Liu, M. Zinnecker, T. Hamaoka, & D. H. Katz (*Biochem.*, 18: 690–697, 1979). The initial MBS derivative of BSA can be prepared exactly as described by Liu, et al., for ovalbumin, using MBS and BSA in pH 7.0 phosphate buffer, and purifying by Sephadex column chromatography. For large batches of the BSA-MBS adduct ("MB-BSA"), dialysis was used more conveniently for the removal of excess reactants. The number of maleimide groups attached to each BSA was determined, by the method outlined by Liu, et al., to be 2.0–2.5, based upon protein content determined by amino acid analysis.

For conjugation to MB-BSA, the Cys-protected peptide described in Example 1 was converted to its free thiol Cys analog. This was done in two steps. First, the Acm group was removed and the thiol oxidized to the symmetrical disulfide by the action of $I_2$, and this symmetrical disulfide was reduced to the free Cys-peptide with dithiothreitol (DTT). Briefly, 30 mg of the Cys-protected peptide described in Example 1 was dissolved in 0.89 ml of 99% acetic acid (1% water) plus one drop of DMF, containing 0.145 mmol $I_2$ in solution. This solution was stirred for 2 hours at room temperature, and the reaction was quenched by the addition of 200 mg moist Zn dust. The suspension was filtered and the solid washed with 50% acetic acid. The filtrate was applied directly to a G-50 Sephadex chromatography column, packed and eluted with 50% acetic acid. Fractions of the first large peak were combined and freeze-dried, giving 16 mg of symmetrical disulfide-linked peptide.

A 7 mg portion of this disulfide peptide dimer was reduced by dissolving in 1 ml pH 6.0 (phosphate) buffer under argon, adding 3 mg dithiothreitol, and stirring for 30 minutes. This solution was applied directly to a short (7 ml total volume) Sephadex G-25 chromatography column, packed and eluted with degassed pH 6.0 buffer at 0° C. The peak eluting with the void volume was collected, avoiding contamination with the slower-running DTT peak, and 100 mg of the MB-BSA was added immediately. This reaction was kept at 0° C. overnight and quenched by the addition of 20 ξl of 2-mercaptoethanol. The quenched reaction was applied to a Sephadex G-100 chromatography column, packed and eluted with pH 6.0 phosphate buffer. The double peak, representing approximately 1:1 BSA-conjugate monomer and higher polymers of BSA-conjugate, was combined and dialyzed against several changes of water for 4 days at 5° C. This material was freeze-dried, giving 104 mg of peptide-BSA conjugate. Amino acid analysis gave a peptide content of approximately 90%, with a loading of 0.68 peptides per BSA unit, based on the Nle amino acid analysis.

| Schedule of Steps for 1 mmol Run | | | |
|---|---|---|---|
| Step | Reagent/Solvent | Vol. M | Mix Time (Min) |
| Coupling: Program 1 | | | |
| 1 | $CH_2Cl_2$ | 4 × 20 | 2 |
| 2 | 40% TFA in $CH_2Cl_2$ | 2 × 20 | 2 |
| 3 | 40% TFA in $CH_2Cl_2$ | 1 × 20 | 25 |
| 4 | $CH_2Cl_2$ | 3 × 20 | 2 |
| 5 | 10% TEA in isopropanol | 2 × 20 | 5 |
| 6 | $CH_2Cl_2$ | 3 × 20 | 2 |
| 7 | 10% TEA in $CH_2Cl_2$ | 2 × 20 | 5 |
| 8 | $CH_2Cl_2$ | 4 × 20 | 2 |
| 9 | Boc-amino acid & HBT (2.5 equiv. each) in 2:1 DMF/$CH_2Cl_2$, mix and hold (no drain) | 1 × 15 | 5 |
| 10 | 0.5 M DCC in $CH_2Cl_2$ | 1 × 5 | 30 |
| 11 | DMF | 1 × 20 | 2 |
| 12 | Methanol | 2 × 20 | 2 |
| 13 | $CH_2Cl_2$ | 2 × 20 | 2 |
| 14 | Methanol | 1 × 20 | 2 |
| 15 | $CH_2Cl_2$ | 1 × 20 | 2 |
| Recoupling: Program 2 | | | |
| 1 | $CH_2Cl_2$ | 3 × 20 | 2 |
| 2 | 10% TEA in $CH_2Cl_2$ | 2 × 20 | 5 |
| 3 | $CH_2Cl_2$ | 3 × 20 | 2 |
| 4 | Boc-amino acid & HBT (2.5 equiv. each) in 2:1 DMF/$CH_2Cl_2$, mix and hold (no drain) | 1 × 15 | 5 |
| 5 | 0.5 M DCC in $CH_2Cl_2$ | 1 × 5 | 30 |
| 6 | DMF | 1 × 20 | 2 |
| 7 | Methanol | 2 × 20 | 2 |
| 8 | $CH_2Cl_2$ | 2 × 20 | 2 |
| 9 | Methanol | 1 × 20 | 2 |
| 10 | $CH_2Cl_2$ | 1 × 20 | 2 |

| Step | Reagent/Solvent | Vol. M | Mix Time (Min) |
|---|---|---|---|
| Coupling Without DCC: Program 3 | | | |
| 1 | $CH_2Cl_2$ | 4 × 20 | 2 |
| 2 | 40% TFA in $CH_2Cl_2$ | 2 × 20 | 2 |
| 3 | 40% TFA in $CH_2Cl_2$ | 1 × 20 | 25 |
| 4 | $CH_2Cl_2$ | 3 × 20 | 2 |
| 5 | 10% TEA in isopropanol | 2 × 20 | 5 |
| 6 | $CH_2Cl_2$ | 3 × 20 | 2 |
| 7 | 10% TEA in $CH_2Cl_2$ | 2 × 20 | 5 |
| 8 | $CH_2Cl_2$ | 4 × 20 | 2 |
| 9 | Boc-amino acid active ester or acetic anhydride/ pyridine (2.5 equiv. each) in 2:1 DMF/$CH_2Cl_2$ | 1 × 20 | 60* |
| 10 | DMF | 1 × 20 | 2 |
| 11 | Methanol | 2 × 20 | 2 |
| 12 | $CH_2Cl_2$ | 2 × 20 | 2 |
| 13 | Methanol | 1 × 20 | 2 |
| 14 | $CH_2Cl_2$ | 1 × 20 | 2 |

*Coupling may be run for up to 18 hours in some cases.

| Step | Reagent/Solvent | Vol. M | Mix Time (Min) |
|---|---|---|---|
| Recoupling Without DCC: Program 4 | | | |
| 1 | $CH_2Cl_2$ | 3 × 20 | 2 |
| 2 | 10% TEA in $CH_2Cl_2$ | 2 × 20 | 5 |
| 3 | $CH_2Cl_2$ | 3 × 20 | 2 |
| 4 | Boc-amino acid active ester or acetic anhydride/ pyridine (2.5 equiv. each) in 2:1 DMF/$CH_2Cl_2$ | 1 × 20 | 60* |
| 5 | DMF | 1 × 20 | 2 |
| 6 | Methanol | 2 × 20 | 2 |
| 7 | $CH_2Cl_2$ | 2 × 20 | 2 |
| 8 | Methanol | 1 × 20 | 2 |
| 9 | $CH_2Cl_2$ | 1 × 20 | 2 |

*Coupling may be run for up to 18 hours in some cases.

EXAMPLE 3

Inoculation of Animals with the Synthetic Peptide-Carrier Conjugate

Antibodies were prepared by inoculating groups of guinea pigs intramuscularly on week 0 and 4 and subcutaneously on week 8 with synthetic peptide-bovine serum albumin (BSA) conjugates emulsified 1:1 in complete Freund's adjuvant. The dosage administered to each animal at each inoculation in 1.0 ml was between 0.85 and 2.80 mg of conjugate. The animals were bled two weeks after the third dose and the sera were analyzed for antibody as described in the subsequent examples.

EXAMPLE 4

Analyses of Sera for Anti-Peptide IgG Antibodies

Anti-peptide IgG antibody was measured by testing the guinea pig sera in a standard indirect enzyme-linked immunosorbent assay (ELISA) carried out in polystyrene microtiter plates. Unconjugated synthetic peptide (5 ξ g/ml) in PBS was adsorbed onto the wells (0.1 ml/well) at 4° C. for 18-24 hours, the wells were washed with PBS containing 0.05% Tween-20 (PBS-T), serial four-fold dilutions (1:20-1:1280) of each serum sample, in PBS-T, were added to duplicate wells (0.1 ml/well) and the plates were incubated at 34°-36° C. for one hour. The wells were washed again, commercially available horseradish peroxidase-labelled goat anti-guinea pig IgG antibody was added to each well and the plates were incubated at 34°-36° for one hour. The wells were washed again, substrate (o-phenylenediamine) was added to each well, the color was allowed to develop at room temperature for 30 minutes at which time the reaction was stopped by the addition of 0.1N sulfuric acid, and the optical density (OD) of each well was read at 490 nm. An absorbance ratio (test serum OD/pre-test serum OD) of _2 was defined as a positive reaction.

All the animals developed anti-peptide antibody with titers of _1:320.

EXAMPLE 5

Analysis of Sera for Anti-HSV1 Glycoprotein Reactivity

Anti-*Herpes simplex* virus type 1 (HSV1) glycoprotein antibody was measured as described in Example 4, except the antigen (0.6 ξ g/ml) adsorbed to the plates was HSV1 glycoprotein isolated from virus-infected cells by extraction with Triton X-100 and purification by *Lens culinaris* lectin affinity chromatography.

Some of the inoculated animals developed anti-HSV1 glycoprotein antibody.

In a competition assay, the specificity of the antibody-antigen reactivity was demonstrated by preincubating (1 hour at room temperature and overnight at 4° C.) a 1:40 dilution of the antiserum that titered 1:320 with an equal volume of varying concentrations (0.01, 0.1, 1.0, 10.0 and 100 ξ g/ml) of peptide and then performing the ELISA as described above. The specific competing peptide completely inhibited binding of antibody by HSV1 glycoprotein at concentrations of equal to or greater than 1 ξ g/ml whereas, an heterologous peptide failed to inhibit the reaction at even the highest concentration tested (100 ξ g/ml).

EXAMPLE 6

Analysis of Sera for HSV1 Neutralizing Antibody

*Herpes simplex* virus type 1 (HSV1) neutralizing antibody was measured by testing the guinea pig sera in a standard virus plaque reduction assay commonly used by those skilled in the art. Briefly, serial two-fold dilutions (1:5-1:80) of the guinea pig sera and a diluent control were mixed with an equal volume of HSV1 containing approximately 1000 PFU/ml and the mixtures were incubated at room temperature for an hour. After incubation, the medium was removed from Vero monkey kidney monolayer cell cultures in 60 mm plates, 0.2 ml volumes of the test and virus control mixtures were added per plate (3 plates/test sample) and the plates were incubated at room temperature for 1 hour. After this adsorption period, 1% methyl cellulose in cell culture medium was added to each plate and the cultures were incubated for 5 days at 34° C., in a 5% $CO_2$ atmosphere incubator. At the end of the incubation period, the plates were washed and stained with carbolfuchsin, the plaques were counted and the percent plaque reduction was calculated (PFU of virus control minus PFU of test sample/PFU of virus control).

The animals that were positive for HSV1 glycoprotein antibody in Example 5 were positive for HSV1 neutralizing antibody.

What is claimed is:

1. An immunogenic synthetic peptide having the sequence:

A-B-D-Gly-Asp-Pro-Lys-Pro-Lys-Lys-Asn-Lys-Lys-Pro-Lys-Asn-Pro-E-G-J-K, wherein

A is amino, amino-p-benzoylbenzoyl, N-acetyl or carboxyl;

B is absent, Tyr or Lys;

D is absent or Nle;

E is absent, Thr, Cys or Nle;

G is absent or Pro;

J is absent or Pro;

K is amino or carboxyl, or a pharmaceutically-acceptable salt thereof.

2. An immunogenic synthetic peptide according to claim 1, having the sequence:

A-Thr-Gly-Asp-Pro-Lys-Pro-Lys-Lys-Asn-Lys-Lys-Pro-Lys-Asn-Pro-Thr-Pro-Pro-K.

3. An immun.ogenic synthetic peptide according to claim 1 selected from the group consisting of:

Ac-Tyr-Nle-Gly-Asp-Pro-Lys-Pro-Lys-Lys-Asn-Lys-Lys-Pro-Lys-Asn-Pro-Cys-NH2;

Ac-Lys-Nle-Gly-Asp-Pro-Lys-Pro-Lys-Lys-Asn-Lys-Lys-Pro-Lys-Asn-Pro-Nle-NH2; and

Ac-Lys(BB)-Nle-Gly-AsP-Pro-Lys-Pro-Lys-Lys-Asn-Lys-Lys-Pro-Lys-Asn-Pro-Nle-NH2, wherein BB is p-benzoylbenzoyl.

4. A conjugate comprising an immunogenic synthetic peptide according to claim 1, which is covalently linked through an amino acid residue of the peptide to a carrier protein or synthetic polymer.

5. A conjugate according to claim 4 wherein the amino acid residue is a Lys, Asp, Glu, Tyr or Cys and the carrier protein is a heterologous serum albumin, keyhole limpet hemocyanin or diphtheria toxoid.

6. A conjugate according to claim 4 wherein the amino acid residue is a Lys, Asp, Glu, Tyr, or Cys and the synthetic polymer is poly(D-Glu, D-Lys).

* * * * *